United States Patent
Prinz

(10) Patent No.: US 10,583,152 B2
(45) Date of Patent: Mar. 10, 2020

(54) THERAPEUTIC USE OF A STERILE AQUEOUS OPHTHALMIC SOLUTION

(71) Applicant: Croma-Pharma Gesellschaft M.B.H., Leobendorf (AT)

(72) Inventor: Martin Prinz, Klosterneuburg (AT)

(73) Assignee: CROMA-PHARMA GESELLSCHAFT M.B.H., Leobendorf (AT)

( * ) Notice: Subject to any disclaimer, the term of this patent is extended or adjusted under 35 U.S.C. 154(b) by 0 days.

(21) Appl. No.: 15/769,487

(22) PCT Filed: Oct. 27, 2016

(86) PCT No.: PCT/EP2016/075939
§ 371 (c)(1),
(2) Date: Apr. 19, 2018

(87) PCT Pub. No.: WO2017/072236
PCT Pub. Date: May 4, 2017

(65) Prior Publication Data
US 2018/0303865 A1    Oct. 25, 2018

(30) Foreign Application Priority Data
Oct. 30, 2015 (EP) .................... 15192362

(51) Int. Cl.
| | | |
|---|---|---|
| *A61K 31/722* | (2006.01) | |
| *A61K 47/02* | (2006.01) | |
| *A61K 47/12* | (2006.01) | |
| *A61K 9/00* | (2006.01) | |
| *A61K 9/08* | (2006.01) | |
| *A61P 27/02* | (2006.01) | |

(52) U.S. Cl.
CPC .......... *A61K 31/722* (2013.01); *A61K 9/0048* (2013.01); *A61K 9/08* (2013.01); *A61K 47/02* (2013.01); *A61K 47/12* (2013.01); *A61P 27/02* (2018.01)

(58) Field of Classification Search
CPC ........ A61K 31/722; A61K 47/12; A61K 9/00; A61K 9/08; A61P 27/02
See application file for complete search history.

(56) References Cited

U.S. PATENT DOCUMENTS

| | | | |
|---|---|---|---|
| 5,412,076 A | 5/1995 | Gagnieu | |
| 2011/0118349 A1 | 5/2011 | Garrigue et al. | |
| 2013/0210761 A1* | 8/2013 | Baker ................. | A61K 31/722 514/54 |

FOREIGN PATENT DOCUMENTS

| | | |
|---|---|---|
| EP | 1126881 B1 | 6/2004 |
| EP | 1487508 B1 | 5/2006 |
| WO | 2008/077172 A1 | 7/2008 |
| WO | 2008/094675 A2 | 8/2008 |
| WO | 2009/132226 A1 | 3/2009 |
| WO | 2009/032228 A1 | 10/2009 |
| WO | 2009/132227 A1 | 10/2009 |
| WO | 2011/127144 A1 | 10/2011 |
| WO | 2015/169728 A1 | 11/2015 |

OTHER PUBLICATIONS

Francesko et al., J. Mater.Chem, 2012, 22, 19438-19446.*
Francesco et al., International Journal of Biological Macromolecules, vol. 76, May 2015.*
International Search Report dated Jan. 26, 2017, issued in PCT Application No. PCT/EP2016/07539, filed Oct. 27, 2016.
Written Opinion dated Jan. 26, 2017, issued in PCT Application No. PCT/EP2016/07539, filed Oct. 27, 2016.

* cited by examiner

*Primary Examiner* — Zohreh A Fay
(74) *Attorney, Agent, or Firm* — Workman Nydegger

(57) ABSTRACT

The present invention relates to a sterile aqueous ophthalmic solution comprising N—(N-acetylcysteinyl-)chitosan or a pharmaceutically acceptable salt thereof in a carrier solution, wherein the N—(N-acetylcysteinyl-)chitosan has a content of free thiol groups in an amount of from 80 μmol/g polymer to 280 μmol/g polymer, for use in the treatment of corneal wounds.

20 Claims, 2 Drawing Sheets

THERAPEUTIC USE OF A STERILE AQUEOUS OPHTHALMIC SOLUTION

The present invention relates to the therapeutic use of a sterile ophthalmic solution comprising N—(N-acetylcysteinyl-)chitosan or a pharmaceutically acceptable salt thereof in a carrier solution.

Mechanical corneal injuries are the most common ophthalmic injuries. They are often caused by the impact of external physical forces (e.g. branches, finger nails, make up applicators), which results in damage of small or large parts of the corneal surface. Foreign body-related abrasions are typically caused by pieces of airborne debris (such as pieces of metal, wood, glass, etc.) that have become embedded in the cornea. After removal of the foreign body defects in the corneal epithelium are left behind. Contact lens-related abrasions are defects in the corneal epithelium which are caused by contact lens overuse or the wearing of an improperly fitting, or improperly cleaned contact lens.

Chemical corneal injuries are another reason for corneal trauma. Exposure to alkaline or acidic substances can cause extensive damage to the corneal surface.

Corneal epithelial damage also occurs as a result of intense exposure to ultraviolet light (photokeratitis) due to the failure to use adequate eye protection (e.g. snow blindness). Corneal wounds also occur in consequence of surgery, such as cataract surgery, corneal transplantation, glaucoma filtering surgery, and refractive eye surgery, such as photorefractive keratectomy (PRK) and laser-assisted in situ keratomileusis (LASIK); or as corneal complications of intraocular surgery such as vitrectomy (Hammil, M. Bowes, 2011, Mechanical Injury. In Krachmer, Mannis et al. (editors): Cornea [$3^{rd}$ edition] Elsevier Inc.: 1169-1185).

Recurrent corneal erosions are characterised by repeated episodes of corneal epithelial breakdown. They can be caused by corneal dystrophies such as epithelial basement membrane dystrophy or they can be the result of corneal minor trauma or abrasion (Steele, Chris, 1999, The role of therapeutic contact lenses in corneal wound healing, Optometry today (October 8): 36-40). The breakdown or loss of the epithelial layer leads to failures in the corneal surface integrity. Corneal wounds related to corneal erosions are thus mainly epithelial damages. Epithelial defects that do not heal over a period of one or two weeks or heal and break down repeatedly are for example non-healing corneal epithelial defects, persistent corneal epithelial defects, slow-healing corneal epithelial defects, and neuropathic (neurotrophic) epithelial defects.

Another epithelial defect with typical scattered, fine, punctate corneal epithelial loss or damage is a so called superficial punctate keratitis (SPK). This corneal inflammation may be a result of various causes such as viral conjunctivitis (most commonly adenovirus), blepharitis, keratoconjunctivitis sicca, trachoma, chemical burns, ultraviolet (UV) light exposure (e.g. welding arcs, sunlaps, snow glare), contact lens overwear, systemic drugs (e.g. adenine arabinoside), topical drugs or preservation toxicity, and peripheral facial nerve palsy (including Bell's palsy). Thus, the SPK may be caused by infections as well as non-infectious reasons.

The treatment of non-infectious corneal wounds has three aims: alleviation of the patient's symptoms via systemic and/or topical administration of pain killers; prevention of infections (if deemed necessary) via topical instillation of antibiotics; and protection of the corneal epithelium. Surgical procedures such as corneal transplantation typically require additional medication for the postoperative phase; however eye drops for the protection and lubrication of the corneal surface are part of the therapy.

Protection of the corneal epithelium is the primary treatment goal after corneal epithelial injuries in order to allow epithelial regeneration and the reestablishment of an intact ocular surface. Current treatment options include the use of ocular lubricants, therapeutic soft contact lenses (bandage lenses) or patching of the eye. Both contact lenses and eye patches can cause ocular discomfort for the patient and may increase healing time and the risk of microbial keratitis. Consequently, their use has to be closely monitored by an eye care practitioner. In the context of to eye patches also tissue engineering is investigated. An artificial blend membrane including hydroxyethyl chitosan, gelatine and chondroitin sulphate seeded with corneal epithelial cells and transplanted on mechanically damaged corneal epithelium was reported to reduce the size of the damaged area at days 2 to 4 post-surgery in rabbits (Liang et al., 2014, Tissue-engineered membrane based on chitosan for repair of mechanically damaged corneal epithelium, Journal of Materials Science: Materials in Medcine (25): 2163-2171). Formulations containing hyaluronic acid are commonly used as ocular lubricants. They were reported to enhance corneal epithelial healing when applied 4 times daily during the acute phase of healing (Stiebel-Kalish et al., 1998, A comparison of the effect of hyaluronic acid versus gentamicin on corneal epithelial healing, Eye (12): 829-833). In case of recurrent corneal erosions lubricant therapy has to be continued after healing of the abrasion as a prophylactic measure for a minimum of 6 months (Steele, Chris, 1999, The role of therapeutic contact lenses in corneal wound healing, Optometry today (October 8): 36-40).

Chitosan has been widely used as topical dressing in the management of skin wounds (Dai, Tanaka et al., 2011, Chitosan preparations for wounds and burns: antimicrobial and wound-healing effects, Expert Rev Anti Infect Ther (9): 857-879). Also the use of thiolated carbohydrates (including thiolated chitosan) was proposed for the preparation of wound dressings (EP1487508 Johnson & Johnson "Therapeutic compositions comprising modified polysaccharides").

It was found that eye drops containing 1.5% chitosan HCl had similar effects to recombinant bovine basic fibroblast growth factor eye drops on promoting the corneal epithelial healing process in a rabbit model. Eye drops applied three times a day containing 0.5% chitosan HCl displayed these promotive effects to a significantly lesser degree and performed only slightly better than the negative control (Yonghon Xu et al. 2009, Promotive Effects of CH-HCL Chitosan Solution on Epithelial Corneal Abrasion in Rabbits, Wuhan University Journal Medical Section 30(2):173-176). However, the reports of the effects of chitosan on corneal wound healing are contradictory. A 1% solution of chitosan failed to improve corneal wound healing when applied three times a day for 3 weeks in a study using a rabbit model (Sall, Kreter et al., 1987, The effect of chitosan on corneal wound healing, Ann Ophthalmol (19): 31-33). Another research group reported that 0.5% solutions of chitosan stimulated corneal wound healing after 24 h incubation of rabbit corneas in organ culture (Cui et al., 2014, Chitosan promoted the corneal epithelial wound healing via activation of ERK MAPK Pathway, Invest. Ophthalmol. Vis. Sci. 55(13):499).

WO2011/127144 discloses the use of derivatized chitosans for a number of different wound healing applications, including the use of a chitosan-arginine polymer for the treatment of corneal wounds. In an alkali burn model of the rabbit cornea the 4 times daily application of a formulation containing a chitosan-arginine derivative for 9 days decreased inflammation and accelerated wound healing. Another mucoadhesive polymer, larch arabinogalactan, was reported to significantly increase the healing rate of corneal wounds in comparison to the vehicle control when applied as 5% solution 3 times daily for a time period of 3 days (Burgalassi, Nicosia et al., 2011, Arabinogalactan as active compound in the management of corneal wounds: in vitro toxicity and in vivo investigations on rabbits, Curr Eye Res (36): 21-28).

Thiolation of polymers has been disclosed to further increase their mucoadhesive properties. EP 1126881 B1 discloses a mucoadhesive polymer comprising at least one non-terminal thiol group. The use of thiolated polysaccharides for preparing an implant for tissue augmentation is disclosed in WO 2008/077172, wherein said thiolated polymers are characterised by the formation of disulfide bonds which leads to a stabilisation of the polymeric network. The priority application of WO 2008/077172, A 2136/2006, discloses further application fields for thiolated polymers.

Modification of chitosan by covalent attachment of thiol group bearing ligands (i.e., thiolation) has been disclosed. It has also been disclosed that thiolation increases the mucoadhesive properties of chitosan (Kast and Bernkop-Schnurch, 2001, Thiolated polymers—thiomers: development and in vitro evaluation of chitosan-thioglycolic acid conjugates, Biomaterials (22): 2345-2352; Bernkop-Schnurch, Hornof et al., 2004, Thiolated chitosans, Eur J Pharm Biopharm (57): 9-17; Bernkop-Schnurch, 2005, Thiomers: a new generation of mucoadhesive polymers, Adv Drug Deliv Rev (57): 1569-1582; Schmitz, Grabovac et al., 2008, Synthesis and characterization of a chitosan-N-acetyl cysteine conjugate, Int J Pharm (347): 79-85). The antimicrobial efficacy of some thiolated chitosans was evaluated as well (WO2009132226 A1; WO2009132227 A1; WO2009132228 A1; Geisberger, Gyenge et al., 2013, Chitosan-thioglycolic acid as a versatile antimicrobial agent, Biomacromolecules (14): 1010-1017)

N-acetylcysteine (NAC) is a derivative of the thiol group bearing amino acid L-cysteine. NAC is a reducing agent with antioxidative activity. It is also well known for its ability to reduce mucus viscosity by reducing mucin disulfide bonds. Due to these mucolytic properties NAC is widely used to reduce mucus viscosity in broncho-pulmonary disorders with excessive mucus production. Topical ophthalmic formulations containing the mucolytic and antioxidant agent NAC are used for the treatment of corneal diseases such as meibomian gland dysfunction and DES (Lemp, 2008, Management of dry eye disease, Am J Manag Care (14): S88-101; Akyol-Salman, Azizi et al., 2010, Efficacy of topical N-acetylcysteine in the treatment of meibomian gland dysfunction, J Ocul Pharmacol Ther (26): 329-333). EP 0 551 848 B1 discloses an ophthalmic pharmaceutical composition for the treatment of DES containing NAC in a concentration between 3% and 5% (w/v) and polyvinylalcohol. It has been disclosed that thiolation of chitosan using NAC increases its ocular residence time on rabbit eyes when compared with non-thiolated chitosan (Dangl, Hornof et al., 2009, In vivo Evaluation of Ocular Residence Time of $^{124}$I-labelled Thiolated Chitosan in Rabbits Using MicroPET Technology, ARVO Meeting Abstracts (50): 3689).

It has been disclosed that N—(N-acetylcysteinyl-)chitosan HCl has some beneficial effect on the ocular surface of the mouse eye in mouse dry eye models (Hongyok, Chae et al., 2009, Effect of chitosan-N-acetylcysteine conjugate in a mouse model of botulinum toxin B-induced dry eye, Arch Ophthalmol (127): 525-532; Hornof, Goyal et al., 2009, Thiolated Chitosan for the Treatment of Dry Eye—Evaluation in Mice Using the Controlled-Environment Chamber Model, ARVO Meeting Abstracts (50): 3663; Hoeller et al., 2011, Safety And Tolerability Of Chitosan-N-acetylcysteine Eye Drops In Healthy Young Volunteers, arvo annual meeting abstract search and program planner; Garhofer et al., 2011 Chitosan-N-Acetylcaxteine Eye Drops, Cataract & Refractive Surgery Today Europe, 49-50).

Further publications reviewing and discussing various uses of thiolated polymers are listed below:

Hornof et al., Mucoadhesive ocular insert based on thiolated poly(acrylic acid): development and in vivo evaluation in humans; Journal of Controlled Release 89 (2003) 419-428; Hornof, M., In vitro and in vivo evaluation of novel polymeric excipients in the ophthalmic field, Thesis, University of Vienna, 2003; Bernkop-Schnurch et al., Permeation enhancing polymers in oral delivery of hydrophilic macromolecules: Thiomer/GSH systems, J. Contr. Release 93(2003) 95-103; M. Hornof et al., In Vitro Evaluation of the Permeation Enhancing Effect of Polycarbophil-Cystein Conjugates on the Cornea of Rabbits, J. Pharm. Sci. 91 (12) 2002, 2588-2592; and Clausen et al., The Role of Glutathione in the Permeation Enhancing Effect of Thiolated Polymers, Pharm. Res. 19 (5) 2002, 602-608; Yamashita et al., Synthesis and Evaluation of Thiol Polymers, J. Macromol. Sc. 26 (1989), 9, 1291-1304; Zheng et al., Disulfide Cross-Linked Hyaluronan Hydrogels, Biomacromolecules 3 (6) 2002, 1304-1311; Wang et al., Chitosan-NAC Nanoparticles as a Vehicle for Nasal Absorption Enhancement of Insulin, J. Biomed Mater Res Part B: Appl Biomater 88B: 150-161, 2009; WO 2008/094675 A2; U.S. Pat. No. 5,412, 076 A.

WO 2015/169728 discloses a sterile aqueous ophthalmic solution comprising about 0.05% to about 0.5% (w/w) of N—(N-acetylcysteinyl-)chitosan or a pharmaceutically acceptable salt thereof in a carrier solution, wherein the N—(N-acetylcysteinyl-)chitosan has a content of free thiol groups in an amount of from 80 µmol/g polymer to 280 µmol/g polymer, and the use of said solution for the treatment of dry eye syndrome.

It is an object of the present invention to provide a pharmaceutical preparation suitable for the treatment of corneal wounds.

This object is solved by a sterile aqueous ophthalmic solution comprising N—(N-acetylcysteinyl-)chitosan or a pharmaceutically acceptable salt thereof in a carrier solution, wherein the N—(N-acetylcysteinyl-)chitosan has a content of free thiol groups in an amount of from 80 µmol/g polymer to 280 µmol/g polymer, for use in the treatment of corneal wounds.

Preferred embodiments of the present invention are listed in the dependent claims.

SHORT DESCRIPTION OF THE DRAWINGS

DETAILED DESCRIPTION OF THE INVENTION

Figure 1:
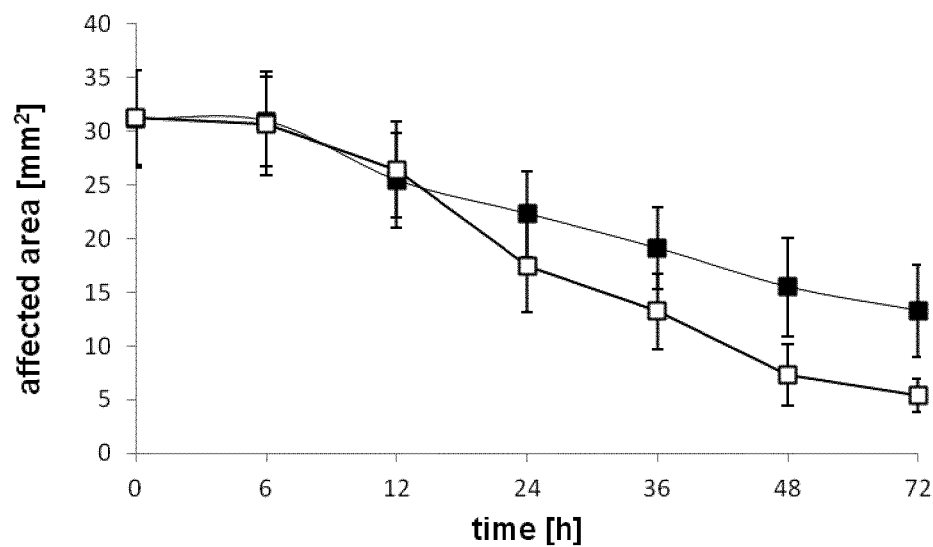
FIG. 1 shows the results of the evaluation of a solution containing 0.1% N—(N-acetylcysteinyl-)chitosan in a corneal wound healing model.
Figure 1:
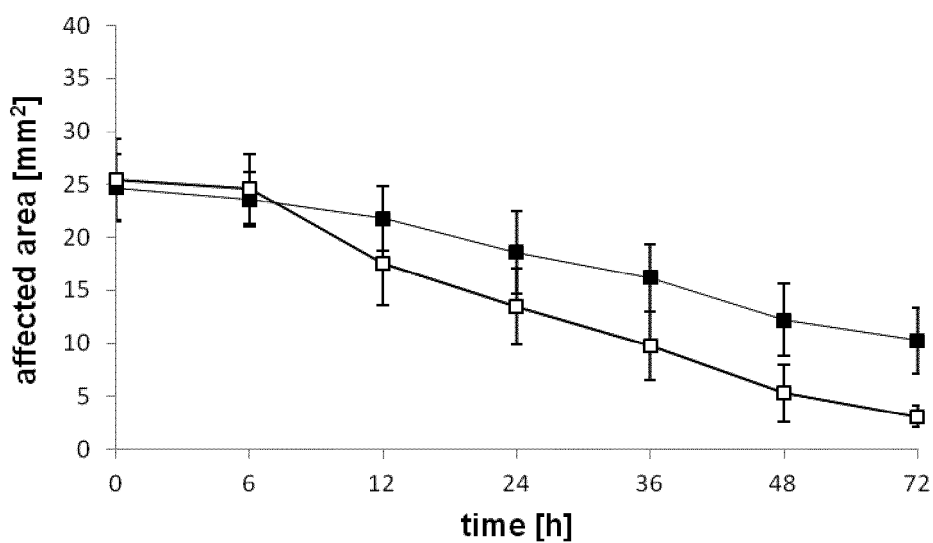

Surprisingly, a sterile aqueous ophthalmic solution comprising N—(N-acetylcysteinyl-)chitosan or a pharmaceutically acceptable salt thereof in a carrier solution, wherein the N—(N-acetylcysteinyl-)chitosan has a content of free thiol groups in an amount of from 80 µmol/g polymer to 280 µmol/g polymer, has been found to be effective in the treatment of corneal wounds.

In a preferred embodiment, said corneal wound may be a non-infectious wound.

In another preferred embodiment, said corneal wound may also be related to corneal erosions.

Ophthalmic solutions used according to the present invention are particularly suitable in treatment of corneal erosions. Among other factors recurrent corneal erosions can be caused by corneal dystrophies, such as epithelial basement membrane dystrophy (Cogan's dystrophy), which affect the integrity of corneal epithelium.

Further, said corneal wound may also be an epithelial defect. For example, the epithelial defect may be selected from the group consisting of non-healing corneal epithelial defects, persistent corneal epithelial defects, slow-healing corneal epithelial defects, and neuropathic (neurotrophic) epithelial defects.

In another embodiment, the corneal wound may be related to a superficial punctate keratitis (SPK).

In the following, the term "chitosan-NAC" stands for both N—(N-acetylcysteinyl-)chitosan and pharmaceutically acceptable salts thereof.

Without wishing to be bound by any theory, the beneficial effect of the chitosan-NAC may be due to its improved mucoadhesive properties and consequently increased ocular residence time and its ability to form a protective coating on the ocular surface.

It has been found that the use of chitosan-NAC in the treatment of corneal wound has the additional benefit of requiring less frequent applications of only once or twice daily.

In a preferred embodiment of the present invention the concentration of the N—(N-acetylcysteinyl-)chitosan or said pharmaceutically acceptable salt thereof in said ophthalmic solution is from 0.05 to 0.3% (w/w), preferably from 0.05 to 0.2% (w/w), more preferably 0.08-0.16% (w/w).

Furthermore, said pharmaceutically acceptable salt is preferably selected from the group consisting of salts of organic acids such as acetic, citric, formic and tartaric acid, and salts of mineral acids such as HCl and $H_2SO_4$.

The N—(N-acetylcysteinyl-)chitosan preferably has a content of free thiol groups in an amount of from 105 µmol/g polymer to 250 µmol/g polymer, preferably of from 110 µmol/g polymer to 250 µmol/g polymer, most preferably of from preferably 140 to 250 µmol/g polymer.

The amount of crosslinked thiol groups in the N—(N-acetylcysteinyl-)chitosan may be 30% or less of the total thiol groups therein, preferably 25% or less, most preferably 15% or less.

The amount of free thiol groups immobilised on chitosan-NAC in an aqueous ophthalmic solution can be determined by the skilled artisan in a known way, such as via Ellman's reagent.

In addition to the fact that a high amount of free thiol groups on the chitosan-NAC polymer in the aqueous ophthalmic solution is important, a low amount of crosslinked thiols (disulfides) on the chitosan-NAC polymer in the solution of the present invention is also preferable. During preparation and storage of the aqueous ophthalmic solution crosslinking of thiol groups immobilised on the chitosan-NAC can occur. A low amount of crosslinked thiols present in the formulation is a preferred parameter of the chitosan-NAC polymer formulation of the present invention.

Therefore, according to a preferred embodiment, the amount of crosslinked thiol groups in the N—(N-acetylcysteinyl-)chitosan is 30% or less of the total thiol groups therein, preferably 25% or less, most preferably 15% or less.

Especially, in this preferred embodiment, the amount of crosslinked thiol groups in the N—(N-acetylcysteinyl-)chitosan is 30% or less of the total thiol groups therein, preferably 25% or less, most preferably 20% or less after storage of the solution for at least 12 months at room temperature.

If the amount of crosslinked thiol groups present in the formula was too high, the properties of the aqueous ophthalmic solution could change outside of the desired parameters, for example, the viscosity of the aqueous ophthalmic solution could become too high to be suitable for eye drops.

As explained below in more detail, it has been found that it is possible to produce a chitosan-NAC the thiol groups of which are not or only minimally crosslinked, such as with an amount of crosslinked thiol groups of less than 5%, preferably 4% or less of the total thiol groups. Especially if such a chitosan-NAC is employed for the manufacture of the ophthalmic solution used according to the present invention, the free thiol groups tend to be stable during the entire life cycle of the solution:

Thus, it has been found that upon employing such a chitosan-NAC during production of the formulation the increase of crosslinked thiol groups is <10% of the amount of free thiol groups initially present on the chitosan-NAC raw material. Furthermore, during storage of the solution over 12 months or even 18 months the increase of crosslinked thiol groups is <15% of the amount of free thiol groups initially present in the formulation. Finally, even if a second container of the solution (as defined below) which provides an oxygen barrier is opened, 30 days after opening the increase of crosslinked thiol groups is <15% of the amount of free thiol groups initially present in the formulation before opening.

Essentially the thiolated chitosan ophthalmic formulation used according to the present invention is made according to the following steps:
1. Chitin is isolated from crustaceous shells, such as shrimp or snow crab shells,
2. Chitosan is prepared from chitin through a chemical process that is well known in the art as, for example alkaline deacetylation;
3. The chitosan is thiolated by the covalent attachment of a thiol bearing ligand, such as with the use of N-acetylcysteine as is set forth herein;
4. The chitosan-NAC is then formulated in the form of an aqueous ophthalmic solution as is set forth herein; and
5. The aqueous ophthalmic solution containing chitosan-NAC is then put into a suitable container that would ensure its stability as is set forth herein.

The chitosan-NAC used in the present invention needs to be water soluble in the concentration range useful for the preparation of the aqueous ophthalmic solution and the resulting solutions need to be clear and colorless. Salt formation of chitosan-NAC with organic or anorganic acids increases the aqueous solubility of chitosan. Suitable salts of thiolated chitosan of the present invention include any pharmaceutically acceptable salts with organic acids such as acetic, citric, formic and tartaric acid, as well as mineral acids such as HCl and $H_2SO_4$. The use of a chitosan-NAC hydrochloride salt is a preferred embodiment of the present invention.

What is important is that such reaction pathways and reaction conditions are used that after synthesis and purification essentially all thiol groups immobilised on the chitosan backbone are present in the free form and not in the crosslinked form as disulfides, i.e. are only minimally cross-linked. Virtually all attached thiols in the thiolated chitosan of the present invention are in the form of free thiol groups, i.e. they are not cross-linked. A minimal amount of cross-linking during synthesis is only acceptable as long as the viscosity of the thiolated chitosan remains within the stated parameters and its aqueous solubility is sufficient for the preparation of an aqueous ophthalmic solution.

It has been found that it is possible to manufacture chitosan-NAC with a very low or even zero degree of crosslinking of the thiol groups by exposing the chitosan-NAC to a reducing agent after its synthesis, for example after alkaline hydrolysis of the thioacetyl moieties. The reducing agent may be selected from the group of DTT, TCEP or $NaBH_4$, $NaBH_4$ being preferred. It has, furthermore, been found that the reduction step should be carried out at elevated temperature, such as 30° C. or more or preferably 40° C. or more. Furthermore, high amounts of reducing agents need to be employed, such as with a stoichiometric ratio of reducing agent to the chitosan backbone polymer of 2:1 or more.

Chitosan-NAC polymers with a degree of crosslinked thiol groups of less than 5%, preferably 4% or less of the total thiol groups can be synthesized according to this embodiment.

The viscosity in aqueous solution of the final chitosan-NAC used according to the present invention preferably falls within a certain range, and it was discovered that the viscosity of the chitosan-NAC only falls within this preferred range if during the production of the chitosan-NAC the chitosan-NAC is processed under certain conditions and within certain parameters, particularly according to the reduction conditions stated above, which lead to polymers which are only minimally crosslinked. The viscosity of the resulting product preferably falls within an acceptable range so that the chitosan-NAC will be most useful in the resulting eye drop formulation. Thus, the kinematic viscosity (0.5% in water at 25° C.) of the chitosan-NAC polymer is preferably within the range of about 1 to 15 $mm^2/s$, more preferably within the range of about 2 to 10 $mm^2/s$. If the viscosity is too high, then a useful eye drop solution cannot be made with the preferred concentration range of chitosan-NAC in the formulation, as the polymer will remain as an insoluble viscous mass in the container.

The chitosan-NAC needs to be purified to be useful in the formulation used according to the present invention (such as after step #3 above and, especially, after treatment of the chitosan-NAC with the reducing agent). The chitosan-NAC should be washed in such a way that the resulting product is pure. One known method is disclosed in Kast and Bernkop-Schnurch, 2001, Thiolated polymers—thiomers: development and in vitro evaluation of chitosan-thioglycolic acid conjugates, Biomaterials (22): 2345-2352.

Another method would be washing the chitosan-NAC with polar solvents followed by drying in order to remove the solvents. One preferred solvent is isopropyl alcohol, since it is non-toxic, readily available, and economical, however other solvents, and other alcohols other than isopropyl alcohol could work as well. This washing can be repeated as needed, depending upon the volume of solvent used each time. Preferably the washing and drying step is repeated at least one time.

The drying step can be conducted at room temperature and at standard humidity, but this process can be very time consuming. Therefore, the drying process is preferably conducted at an elevated temperature and/or under reduced pressure. The drying of the chitosan-NAC is preferably conducted at an elevated temperature of at least about 40° C. to about 70° C. and preferably for at least about five hours. A more preferred drying process is conducted at temperatures of at least about 50° C. to about 60° C. for about 10 to 24 hours. One preferred multi-step purification process would be to wash the chitosan-NAC polymer three times with isopropyl alcohol and to recover the solid by centrifugation followed by drying at about 60° C. for about 15 to 20 hours.

The aqueous ophthalmic solution used according to the present invention can contain at least one ophthalmic compatible excipient. Any excipient suitable for example to adjust the tonicity, the viscosity of the solution or to stabilise the pH, to increase the solubility of the active ingredient, to increase ocular comfort after application, or to stabilise the formulation in general, can be employed.

The pH of the aqueous ophthalmic solution is adjusted by adding any physiologically and ophthalmic acceptable pH adjusting acids, bases, or buffers to have a pH within the range of about 5.5 to about 7. A pH much below about 5.5 would be outside of the physiological acceptable parameters (the solution would cause a severe stinging or burning sensation in the eye). At a pH much above 7, forming a stable solution of the chitosan-NAC where it does not precipitate out of solution is difficult. Thus, due to the ease of formulating a stable solution, a pH below 7 is preferred. The preferred pH of the aqueous ophthalmic solution used according to the present invention is between about 5.8 to about 6.8, with a pH of 6.0 to 6.6 being most preferred.

Examples of suitable acids used in the formulation of the present invention include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. A preferred embodiment is a boric acid and sodium borate buffer system, which also contains a polyol such as mannitol to increase buffer capacity at the most preferred pH range of 6.0 to 6.6.

Examples of suitable excipients used in the formulation to increase stability of the formulation include disodium ethylenediaminetetraacetate ($Na_2$-EDTA), sodium metabisulfite, mannitol, polyethylene glycol and the like.

The osmolarity of the topical ophthalmic formulation used in the present invention is generally from about 150 to about 400 milliosmolar (mOsM), more preferably from about 200 to about 350 mOsM, with the osmolarity of about 250 to about 330 mOsM being most preferred. The osmolarity can be adjusted by using appropriate amounts of physiologically and ophthalmic acceptable ionic or non-ionic agents. Sodium chloride is a common osmotic agent. Equivalent amounts of one or more salts made up of cations such as potassium, ammonium and the like and anions such as chloride, citrate, ascorbate, borate, phosphate, bicarbonate, sulfate, thiosulfate, bisulfate, and the like can be used in addition to or instead of sodium chloride to achieve osmorality within the above-stated range. Further, non-ionic agents such as mannitol, dextrose, sorbitol, glycerol, glucose and the like can also be used to adjust the osmolarity. Sodium chloride and mannitol are the preferred agents to adjust osmotic pressure.

The ophthalmic formulation can contain lubricants to provide a high ocular comfort level suitable for the regular application necessary in the treatment of DES. There are many types of lubricating agents such as polyvinylpyrrolidone, polyvinylalcohol, liquid polyols, hyaluronic acid and pharmaceutically acceptable salts thereof, lubricin and cellulose derivatives; however preferred agents are polyethylene glycol and hydroxypropyl methylcellulose (HPMC).

In a preferred embodiment, the ophthalmic solution used according to the present invention contains the following excipients in addition to N—(N-acetylcysteinyl-)chitosan hydrochloride:

Boric acid in an amount from 1.0 to 16.0 mg/ml, preferably 8 to 16 mg/ml; Polyethylenglycol 400 in an amount from 0.01 to 5.0 mg/ml, preferably 1 to 5 mg/ml; $Na_2$-EDTA in an amount from 0.01 to 0.5 mg/ml; Mannitol in an amount from 0.01 to 5.5 mg/ml, preferably 0.1 to 4 mg/ml; Sodium chloride in an amount from 0.01 to 9 mg/ml, preferably 1 to 3 mg/ml; and Hydroxypropyl methylcellulose in an amount from 0.01 to 20 mg/ml, preferably 1 to 3 mg/ml.

The ophthalmic solution used according to the present invention has to be sterile and can be sterilized in any suitable manner. One particular preferred sterilization method is sterile filtration. The ophthalmic solution according to the present invention can contain preservatives, such as benzalkonium chloride, although this is less preferred.

The aqueous ophthalmic solution containing chitosan-NAC can be administered to the eyes of a patient by any suitable means for topical administration. This is preferably in the form of an aqueous eye drop solution. This solution can be in a single use container that is sterile until opened and thus does not need to have a preservative, or it can be in the form of a multi-use container that remains sterile after opening or in a multi-use container with a formulation containing a preservative.

The thiol groups of chitosan-NAC polymers tend to form disulfide bonds in aqueous solutions, thus reducing the mucoadhesive properties of chitosan-NAC. It was discovered that this tendency depends on the presence of oxygen in the aqueous ophthalmic solution.

It has been found that it is possible to stabilize the free thiol groups of the chitosan-NAC employed according to the present invention in aqueous solution even more when storing the solution under oxygen-free conditions, or essentially oxygen-free conditions. The oxygen-free atmosphere can be a nitrogen atmosphere, vacuum atmosphere, or an atmosphere consisting of noble gases.

Thus, when the solution is put into a container it should be done so in the absence of oxygen. Further, after the container is filled with the aqueous ophthalmic solution of the present invention, it should remain oxygen free. Therefore, the present invention also contemplates the use of a container that keeps the aqueous ophthalmic solution free from oxygen during storage.

Accordingly, in the present invention preferably an essentially oxygen free container containing the aqueous ophthalmic solution is used. As "essentially oxygen free", an atmosphere with an amount of 1.5% oxygen or less is to be understood. The concentration of dissolved oxygen in solution during production of the formulation and filling into the containers is below 1.0 mg/L, more preferably below 0.5 mg/L, even more preferably in the range of 0.1 mg/L.

In a preferred embodiment, the container is made of a material that is impervious to oxygen such that after filling, the ophthalmic solution remains essentially oxygen free for an extended period of time. Such containers could be glass or glass lined polymers, metal or metal lined polymers. In another preferred embodiment, the container is made of a polymer that has contained therein an oxygen absorber that would prevent oxygen from entering the solution through the walls of the container. Such oxygen absorbers include iron salts, sulfites, ascorbic acid, unsaturated fatty acid salts, metal-polyamide complexes or palladium/$H_2$ based systems. For example, WO 09/32526 discloses a film having an active oxygen barrier layer comprising an oxygen scavenging composition blended of a thermoplastic resin having carbon-carbon double bonds substantially in its main chain, a transition metal salt, and an oxygen barrier polymer with oxygen barrier properties.

Further, the container itself can be manufactured from a gas tight material with an oxygen scavenger embedded and an airless closure system.

In a preferred embodiment, there is provided a first container containing the ophthalmic solution and a second container containing said first container.

Thus, for example, the container that holds the ophthalmic solution of the present invention is itself contained inside of a gas tight sachet or pouch. In particular a sachet or pouch made of aluminium or an aluminium laminate or aluminium composition may contain therein one or more sub-containers (i.e. "first containers") containing the ophthalmic solution according to the invention. The second container, i.e. the sachet or pouch can also contain an additional oxygen absorber (for example PKT KH-20 Pharmakeep® or Stabilox® Oxygen Scavenger) as is used in some standard packaging. Even in the case where the sachet is sealed under vacuum or in an inert atmosphere, the addition of an oxygen absorber can be required in order to remove residual oxygen from the sub-container. The sachet can contain either one or more single dose containers or multi-dose containers, for example five single dose containers per sachet. In the case of the multi-dose container, it must preserve the ophthalmic solution according to the present invention in a sterile condition and in an essentially oxygen free condition.

The chitosan-NAC contained in the container preferably used according to the invention preferably has a content of free thiol groups of from 80 μmol/g polymer to 250 μmol/g polymer, preferably 105 μmol/g polymer to 250 μmol/g polymer after storage of at least 12 months at room temperature. This means that, the free thiol groups remain on the chitosan-NAC and that the resulting formulation is stabile over an extended period of time. This period of time is preferably at least about 12 months, more preferably at least 18 months, and even more preferably at least about 24 months. This long stability preference is due to the fact that some products end up having long storage times and delays in commercial delivery and supply chains that could result in a less stable product falling out of acceptable parameters.

Furthermore, preferably the amount of crosslinked thiol groups in the chitosan-NAC contained in the container is 30% or less of the total thiol groups therein, preferably 25% or less, most preferred 20% or less after being stored for at least 12 months, more preferably at least 18 months. As mentioned above, the stability of the free thiol groups in the solution is especially good if a chitosan-NAC with only a minimal degree of crosslinked thiol groups is employed for manufacturing the solution.

In the above-described embodiment where there is a second container, e.g. a gas tight sachet, containing one or more first container(s), e.g. single use containers made from LDPE, the content of free thiol groups in the solution preferably remains within the range as defined per the present invention after opening of the first container for at least 30 days. The therapeutic time needed for e.g. 5 containers is 5 days, thus this duration of stability is more than sufficient.

As mentioned above, it was found that especially if a chitosan-NAC with only a minimal degree of crosslinked thiol groups is employed for manufacturing the ophthalmic solution of the present invention, the free thiol groups remained stable even after the second container which provides the oxygen barrier was opened, i.e. it was found that 30 days after opening of the second container the increase of crosslinked thiol groups was <15% of the amount of thiol groups initially present in the solution before opening.

In a further preferred embodiment, the ophthalmic solution is applied to a corneal wound twice or once daily.

The present invention also relates to a method of treatment of a non-infectious corneal wound, wherein a sterile aqueous ophthalmic solution comprising N—(N-acetylcysteinyl-)chitosan as defined above is applied to said wound.

EXAMPLES

Example 1: Corneal Wound Healing Model

The aim of this experiment was to evaluate whether an aqueous ophthalmic solution containing 0.1% chitosan-NAC (degree of modification: 209 µM free thiol groups/g polymer) is capable of accelerating the wound healing process in comparison to a control substance consisting of phosphate-buffered saline (PBS). The aqueous ophthalmic solution containing 0.1% (w/w) chitosan-NAC was prepared under inert conditions by dissolving chitosan-NAC in a boric acid buffer solution additionally comprising mannitol, polyethylenglycol 40 and hydroxypropyl methylcellulose (HPMC). The final pH of the solution was 6.4. Female New Zealand white rabbits (Charles River, Ekrath, Germany) with a body weight of 1.7 kg to 2.5 kg were used for the experiment. The animals were kept pair-wise in a controlled environment: artificial day-night rhythm 12/12 hours, 20° C. room temperature, 60% humidity. Water and standard food for rabbits was provided ad libitum.

The animals were studied after a period of at least 2 weeks after delivery to allow for adaptation to the environment.

In a total of 16 animals a defined corneal lesion was induced. The central corneal epithelium was removed with an ophthalmic scalpel carefully avoiding damage to Bowman's layer. The size of the defect was aimed at a diameter of 6 mm. The size of the corneal lesion was characterized by applying ultrahigh-resolution OCT and slit-lamp photography after instillation of fluorescein. Measurements were done at baseline (before incision) and 6, 12, 24, 36, 48 and 72 hours after induction of the corneal lesion. Administration of the eye drops was done every 12 hours throughout the experiments. All experiments were performed under anesthesia which was achieved by intramuscular injection of 25 mg/kg Ketamine and 2 mg/kg Xylazine. As analgesics Metamizol-Sodium and 0.025 mg Fentanyl were administered.

The results of this study are summarized in FIG. 1 which shows the time course of wound healing after application of either chitosan-NAC (white markers) or PBS (Placebo, black markers). On the y-axis the area of the defect is shown. Data were assessed from slit lamp photography after fluorescein staining of corneal lesions (A) or from OCT images (B). Data are presented as means+/−standard deviation. A significantly faster healing rate was observed with eye drops containing chitosan N-acetylcysteine versus placebo ($p<0.05$ each, repeated measures ANOVA). Good agreement was observed between data obtained from the two different techniques.

Example 2 Formation of a Polymeric Network on the Ocular Surface

Human corneal-limbal epithelial (HCLE) cells were maintained in serum-free keratinocyte growth medium (Thermo Fisher Scientific) at 37° C. and 5% $CO_2$ and seeded at 1×105 cells/well into 24-well plates filled with 11 mm ACLAR® coverslip discs. When cells had reached confluence they were treated for 15 minutes with 0.1% (w/w) chitosan-HCl or 0.1% (w/w) chitosan-NAC (degree of modification: 219 µM free thiol groups/gram polymer) diluted in 100 mM Boric acid buffer. Boric acid buffer was also applied to control cells. Next, the polymer solutions were removed and cells were immediately fixed for scanning electron microscopy (SEM) by adding 2.5% glutaraldehyde in 0.06×PHEM buffer (1×PHEM buffer contains 60 mM PIPES, 25 mM HEPES, 10 mM EGTA, and 2 mM $MgCl_2$). Cell monolayers were then post-fixed in 1% aqueous osmium tetroxide (Agar Scientific, Stansted, UK), dehydrated in graded acetone, critical point dried in liquid $CO_2$ (Leica CPD300, Leica Microsystems GmbH, Vienna, Austria), attached to 12 mm aluminum SEM stubs with C-tabs before gold sputter-coated (100 msec) with rotation (Leica sputter coater, Leica Microsystems GmbH, Vienna, Austria), and viewed with a JEOL IT300 SEM at 15 kV. All images were taken with a secondary electron detector at 300× magnification.

Figure 2:
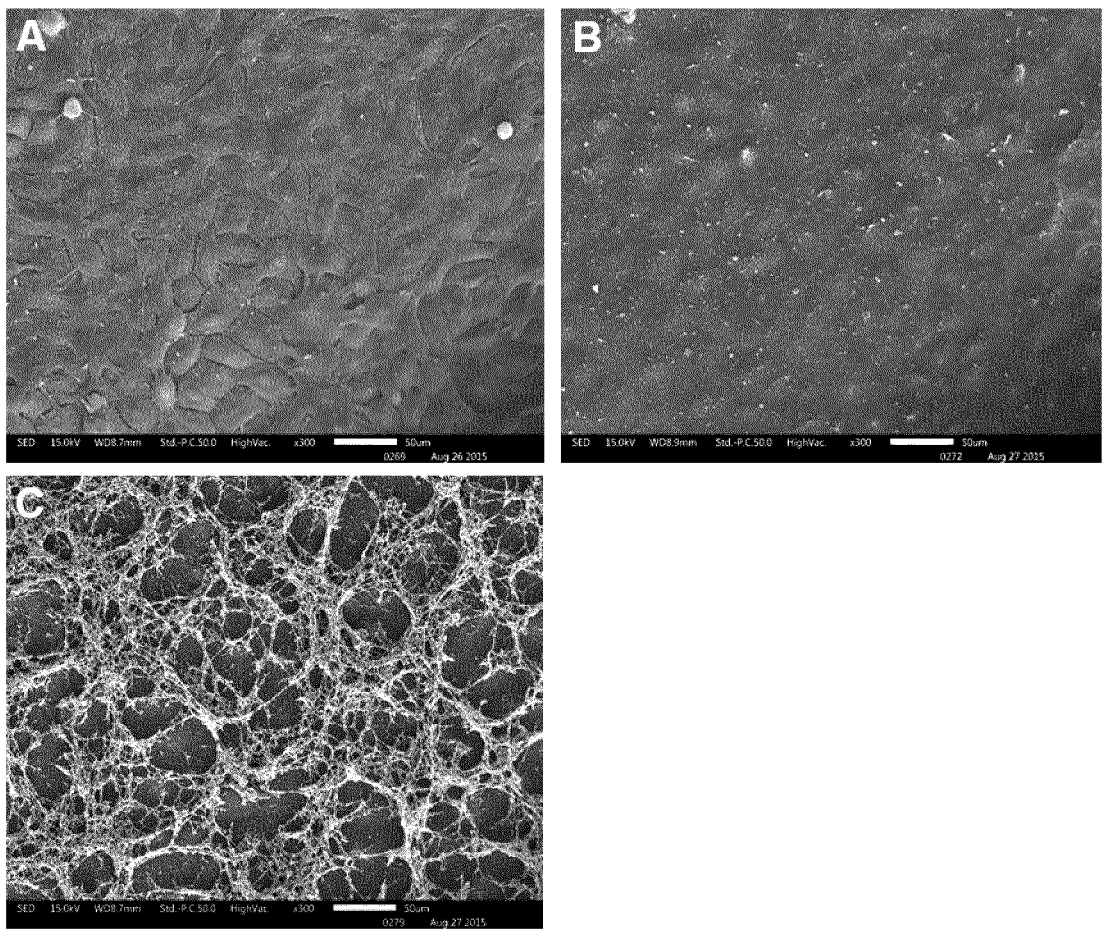
FIG. 2 shows the results of scanning electron microscopy of human corneal-limbal epithelial cells incubated with 0.1% chitosan-HCl (B) or 0.1% N—(N-acetylcysteinyl-) chitosan (C). Non-treated confluent control cells are shown for comparison (A).

The results are shown in FIG. 2 which shows the scanning electron microscopy of human corneal-limbal epithelial cells incubated with 0.1% (w/w) chitosan-HCl (B) or 0.1% (w/w) chitosan-NAC (C). Non-treated confluent control cells are shown for comparison (A). FIG. 2C clearly shows the formation of a polymeric network on the cell surface after application of chitosan-NAC solutions. This effect is not observed in control cells (FIG. 2A) and in cells treated with chitosan-HCl (FIG. 2B).

Example 3 Case Study

A male patient (57 years old) suffering from extremely severe atopic dermatitis and multiple times recurrent herpetic keratitis had to undergo emergency perforating keratoplasty because of a perforation. He developed a post-surgical infection of the transplant that could be controlled by antibiotics. However, he suffered from a persisting epithelial defect that did not heal for months despite of multiple different medications (topical medications: Vigamox 4×/d, Dexa EDO 2×/d and Vismed hourly; oral medications: Valtrex 1-0-1, Myfortic 360 mg 2-0-2, Decortin H 12.5 mg/day).

After additional ocular application of an aqueous ophthalmic solution containing 0.1% chitosan-NAC (degree of modification: 212 µM free thiol groups/g polymer) once daily for 7 days the defect in the corneal epithelium was healed.

Example 4 Case Study

A male patient (31 years, contact lens wearer) with red and painful eyes was diagnosed with bilateral superficial punctate keratitis (SPK) and mild ciliary injection. The initial treatment with levofloxacin eye drops lead to an improvement of the symptoms over the next 3 weeks but the SPK remained. Predsol 0.5% eyedrops 3×/day were added to the medication. The clinical findings remained the same a week later and Celluvisc 0.5% eyedrops every 2 hours and Doxycyline 100 mg were further added to the medication.

After a month the clinical findings were still not improved. Repeated treatments with Azyter eyedrops did also not result in any marked improvement of the SPK. After treatment with Celluvisc eyedrops and tea tree oil for lid hygiene for a month the patient's symptoms worsened again. All previous medications were stopped.

After treatment with an aqueous ophthalmic solution containing 0.1% chitosan-NAC (degree of modification: 212 µM free thiol groups/g polymer) once daily for 5 days patient's symptoms markedly improved and the remaining SPK was only minimal.

The invention claimed is:

1. A method of treating a corneal wound, comprising
   applying to a corneal wound a sterile aqueous ophthalmic solution comprising N—(N-acetylcysteinyl-) chitosan or a pharmaceutically acceptable salt thereof in a carrier solution,
   wherein the N—(N-acetylcysteinyl-) chitosan has a content of free thiol groups in an amount of from 80 µmol/g polymer to 280 µmol/g polymer,
   wherein the ophthalmic solution treats the corneal wound.

2. The method according to claim 1, wherein the corneal wound is related to corneal erosions.

3. The method according to claim 1, wherein the corneal wound is an epithelial defect selected from the group consisting of non-healing corneal epithelial defects, persistent corneal epithelial defects, slow-healing corneal epithelial defects, and neuropathic (neurotrophic) epithelial defects.

4. The method according to claim 1, wherein the corneal wound is related to a superficial punctate keratitis.

5. The method according to claim 1, wherein the concentration of the N—(N-acetylcysteinyl-) chitosan or said pharmaceutically acceptable salt thereof in said solution is from 0.05 to 0.3% (w/w).

6. The method according to claim 1, wherein said pharmaceutically acceptable salt is selected from the group consisting of salts of organic acids and salts of mineral acids.

7. The method according to claim 1, wherein the N—(N-acetylcysteinyl-) chitosan has a content of free thiol groups in an amount of from 105 µmol/g polymer to 250 µmol/g polymer.

8. The method according to claim 1, wherein the amount of crosslinked thiol groups in the N—(N-acetylcysteinyl-) chitosan is 30% or less of the total thiol groups therein.

9. The method according to claim 1, wherein said ophthalmic solution is applied to a corneal wound twice daily.

10. The method according to claim 1, wherein said corneal wound is a non-infectious wound.

11. The method according to claim 5, wherein the concentration of the N—(N-acetylcysteinyl-) chitosan or said pharmaceutically acceptable salt thereof in said solution is from 0.05 to 0.2% (w/w).

12. The method according to claim 5, wherein the concentration of the N—(N-acetylcysteinyl-) chitosan or said pharmaceutically acceptable salt thereof in said solution is from 0.08-0.16% (w/w).

13. The method according to claim 6, wherein said pharmaceutically acceptable salt is a salt of an organic acids selected from acetic acid, citric acid, formic acid, or tartaric acid.

14. The method according to claim 6, wherein said pharmaceutically acceptable salt is a salt of a mineral acid selected from HCl or $H_2SO_4$.

15. The method according to claim 7, wherein the N—(N-acetylcysteinyl-) chitosan has a content of free thiol groups in an amount of from 110 µmol/g polymer to 250 µmol/g polymer.

16. The method according to claim 7, wherein the N—(N-acetylcysteinyl-) chitosan has a content of free thiol groups in an amount of from 140 µmol/g polymer to 250 µmol/g polymer.

17. The method according to claim 8, wherein the amount of crosslinked thiol groups in the N—(N-acetylcysteinyl-) chitosan is 25% or less of the total thiol groups therein.

18. The method according to claim 8, wherein the amount of crosslinked thiol groups in the N—(N-acetylcysteinyl-) chitosan is 15% or less of the total thiol groups therein.

19. The method according to claim 1, wherein said ophthalmic solution is applied to a corneal wound once daily.

20. A method of treating a corneal wound, comprising
    applying to a non-infectious corneal wound once or twice daily in a subject in need thereof a sterile aqueous ophthalmic solution comprising N—(N-acetylcysteinyl-) chitosan or a pharmaceutically acceptable salt thereof in a carrier solution,
    wherein the N—(N-acetylcysteinyl-) chitosan has a content of free thiol groups in an amount of from 80 µmol/g polymer to 280 µmol/g polymer,
    wherein the ophthalmic solution treats the non-infectious corneal wound.

* * * * *